United States Patent [19]

Yoshitomi et al.

[11] Patent Number: 5,559,093
[45] Date of Patent: Sep. 24, 1996

[54] N-TERMINALLY TRUNCATED HST-1 IS A PLATELET-INCREASING FACTOR

[75] Inventors: Sumie Yoshitomi, Osaka; Tsutomu Kurokawa, Kawanishi; Koichi Igarashi, Kyoto, all of Japan

[73] Assignee: Takeda Chemical Industries, Ltd., Osaka, Japan

[21] Appl. No.: 102,691

[22] Filed: Aug. 5, 1993

[30] Foreign Application Priority Data

Aug. 5, 1992 [JP] Japan ................................. 4-208746

[51] Int. Cl.⁶ .................. A61K 38/18; C07K 14/495; C07K 14/53; C12P 21/06
[52] U.S. Cl. .................. 514/2; 530/399; 435/69.1; 435/69.8
[58] Field of Search .................. 530/399; 435/69.1, 435/69.8; 514/2

[56] References Cited

FOREIGN PATENT DOCUMENTS

0421455A1 4/1991 European Pat. Off. .
0503297A1 9/1992 European Pat. Off. .

OTHER PUBLICATIONS

Iida et al. 1992 Oncogene 7(2): 303–309

Primary Examiner—Charles L. Patterson, Jr.
Assistant Examiner—Karen Cochrane Carlson
Attorney, Agent, or Firm—David G. Conlin; Ronald I. Eisenstein

[57] ABSTRACT

A method of increasing platelets in mammals which comprises administering to mammals an effective amount of a heparin-binding secretory transforming factor 1 protein (hst-1) having an N-terminal deletion of 27 amino acids.

1 Claim, 8 Drawing Sheets

```
                                    10                                      20
Met Ser Gly Pro Gly Thr Ala Ala Val Ala Leu Leu Pro Ala Val Leu Leu Ala Leu Leu 30                                      40
Ala Pro Trp Ala Gly Arg Gly Gly Ala Ala Ala Pro Thr Ala Pro Asn Gly Thr Leu Glu 50                                      60
Ala Glu Leu Glu Arg Arg Trp Glu Ser Leu Val Ala Leu Ser Leu Ala Arg Leu Pro Val 70                                      80
Ala Ala Gln Pro Lys Glu Ala Ala Val Gln Ser Gly Ala Gly Asp Tyr Leu Leu Gly Ile 90                                      100
Lys Arg Leu Arg Arg Leu Tyr Cys Asn Val Gly Ile Gly Phe His Leu Gln Ala Leu Pro 110                                     120
Asp Gly Arg Ile Gly Gly Ala His Ala Asp Thr Arg Asp Ser Leu Leu Glu Leu Ser Pro 130                                     140
Val Glu Arg Gly Val Val Ser Ile Phe Gly Val Ala Ser Arg Phe Phe Val Ala Met Ser 150                                     160
Ser Lys Gly Lys Leu Tyr Gly Ser Pro Phe Phe Thr Asp Glu Cys Thr Phe Lys Glu Ile 170                                     180
Leu Leu Pro Asn Asn Tyr Asn Ala Tyr Glu Ser Tyr Lys Tyr Pro Gly Met Phe Ile Ala 190                                     200
Leu Ser Lys Asn Gly Lys Thr Lys Lys Gly Asn Arg Val Ser Pro Thr Met Lys Val Thr

His Phe Leu Pro Arg Leu
```

FIG. 1

```
                                            1
                        Pro Thr Ala Pro Asn Gly Thr Leu Glu
    10                      20
Ala Glu Leu Glu Arg Arg Trp Glu Ser Leu Val Ala Leu Ser Leu Ala Arg Leu Pro Val
    30                      40
Ala Ala Gln Pro Lys Glu Ala Ala Val Gln Ser Gly Ala Gly Asp Tyr Leu Leu Gly Ile
    50                      60
Lys Arg Leu Arg Arg Leu Tyr Cys Asn Val Gly Ile Gly Phe His Leu Gln Ala Leu Pro
    70                      80
Asp Gly Arg Ile Gly Gly Ala His Ala Asp Thr Arg Asp Ser Leu Leu Glu Leu Ser Pro
    90                      100
Val Glu Arg Gly Val Val Ser Ile Phe Gly Val Ala Ser Arg Phe Phe Val Ala Met Ser
    110                     120
Ser Lys Gly Lys Leu Tyr Gly Ser Pro Phe Phe Thr Asp Glu Cys Thr Phe Lys Glu Ile
    130                     140
Leu Leu Pro Asn Asn Tyr Asn Ala Tyr Glu Ser Tyr Lys Tyr Pro Gly Met Phe Ile Ala
    150                     160
Leu Ser Lys Asn Gly Lys Thr Lys Lys Gly Asn Arg Val Ser Pro Thr Met Lys Val Thr
    170
His Phe Leu Pro Arg Leu
```

FIG. 2

Pro Val

Ala Ala Gln Pro Lys Glu Ala Ala Val Gln Ser Gly Ala Gly Asp Tyr Leu Leu Gly Ile

Lys Arg Leu Arg Arg Leu Tyr Cys Asn Val Gly Ile Gly Phe His Leu Gln Ala Leu Pro

Asp Gly Arg Ile Gly Gly Ala His Ala Asp Thr Arg Asp Ser Leu Leu Glu Leu Ser Pro

Val Glu Arg Gly Val Val Ser Ile Phe Gly Val Ala Ser Arg Phe Phe Val Ala Met Ser

Ser Lys Gly Lys Leu Tyr Gly Ser Pro Phe Phe Thr Asp Glu Cys Thr Phe Lys Glu Ile

Leu Leu Pro Asn Asn Tyr Asn Ala Tyr Glu Ser Tyr Lys Tyr Pro Gly Met Phe Ile Ala

Leu Ser Lys Asn Gly Lys Thr Lys Lys Gly Asn Arg Val Ser Pro Thr Met Lys Val Thr

His Phe Leu Pro Arg Leu

FIG. 3

N-TERMINALLY TRUNCATED HST-1 IS A PLATELET-INCREASING FACTOR

FIELD OF THE INVENTION

The present invention relates to a platelet-increasing agent containing a heparin-binding secretory transforming factor (hst-1) or a mutein thereof.

BACKGROUND OF THE INVENTION

Platelets play an important role in the promotion of thrombus formation and blood coagulation, which takes place in the course of hemostasis, in which the bleeding caused by the breakage of blood vessels naturally stops. In humans, the platelets are released in the blood from megakaryocytes produced by differentiation from myeloid stem cells through megakaryocyte precursor cells.

A reduction in the number of platelets can be caused by thrombocytopenia, or by administration of anticancer drugs or irradiation with radioactive rays in treating cancers, which can result in serious consequences. However, no effective platelet-increasing agent has so far been discovered.

Heparin-binding secretory transforming factor gene (hst-1 gene) is a transforming gene, which has been isolated from the tissue of human stomach cancer [H. Sakamoto et al., *Proc. Natl. Acad. Sci.*, U.S.A., 83, 3997 (1988)]. The gene product thereof shows some homology to fibroblast growth factor (FGF), one of cell growth factors, in structure and biological activity [T. Yoshida et al., *Proc. Natl. Acad. Sci.*, U.S.A., 84, 7305 (1987) and K. Miyagawa et al., *Oncogene*, 3, 383 (1988)]. The hst-1 gene has been isolated not only from stomach cancer tissue, but also from the tissues of colon cancer, hepatic cancer and Kaposi sarcoma of patients suffering AIDS [T. Koda et al., *Jpn. J. Cancer Res.* (Gann), 78, 325 (1987), H. Nakagawa et al., *Jpn. J. Cancer Res.* (Gann), 78, 651 (1987), Y. Yuasa et al., *Jpn. J. Cancer Res.* (Gann), 78, 1035 (1987), and P. Delli Bovi et al., *Cell*, 50, 729 (1987)]. This gene has been clasified along with basic FGF, acidic FGF, int-2 gene, etc. as forming the FGF faimily. The gene isolated from the above-mentioned Kaposi sarcoma, which is identical to hst-1 is also called K-FGF.

The nucleotide sequence of the hst-1 gene has already been reported [M. Taira et al., *Proc. Natl. Acad. Sci.* U.S.A., 84, 2980 (1987), and T. Yoshida et al., *Proc. Natl. Acad. Sci.* U.S.A., 84, 7305 (1987)]. These reports provide the gene product deduced therefrom and the constituent amino acids of the hst-1 protein.

No effective platelet-increasing agent has so far been discovered, and the properties and biological activity of the hst-1 are unknown in many respects. It would be desirable to have an effective platelet-increasing agent. It would also be desirable to have such an agent that could readily be prepared.

SUMMARY OF THE INVENTION

The present inventors have extesively searched for substances whose cells produce factors that exhibit effective platelet-increasing action on known cytokines. As a result, the present inventors have discovered that hst-1 prepared by the recombinant DNA technique or hst-1 muteins that are similar therewith in activity show growth promoting activity for megakaryocytes (MK-CSF activity) sufficient to increase the number of peripheral platelets. Further investigations based on these findings resulted in the present invention.

According to the present invention, there are provided (1) a method of increasing platelets in mammals which comprises administering to mammals an effective amount of a heparin-binding secretory transforming factor 1 protein (hst-1) or a mutein thereof; (2) the method as described in (1) in which said mutein is a deletion type mutein; (3) the method as described in (2) wherein said mutein is lacking at least one amino acid or more amino acids from the N-terminus of SEQ ID NO:2; (4) the method as described in (2) wherein said mutein is lacking up to 47 amino acids of the N-terminal sequence of SEQ ID NO:2; (5) the method as described in (2) wherein said mutein is lacking up to 27 amino acids of the N-terminal sequence of SEQ ID NO:2; and (6) the method as described in (2) wherein said-mutein is lacking 27 amino acids of the N-terminal sequence of SEQ ID NO:2.

BRIEF DESCRIPTION OF THE DRAWINGS

FIG. 1 shows an amino acid sequence deduced from a coding region of hst-1 containing a leader sequence constituting an open reading frame of hst-1 cDNA;

FIG. 2 shows an amino sequence of a mature protein of hst-1;

FIG. 3 shows an amino acid sequence of hst-1 mutein N27 obtained in Reference Example;

DESCRIPTION OF THE PREFERRED EMBODIMENTS

Figure 4:
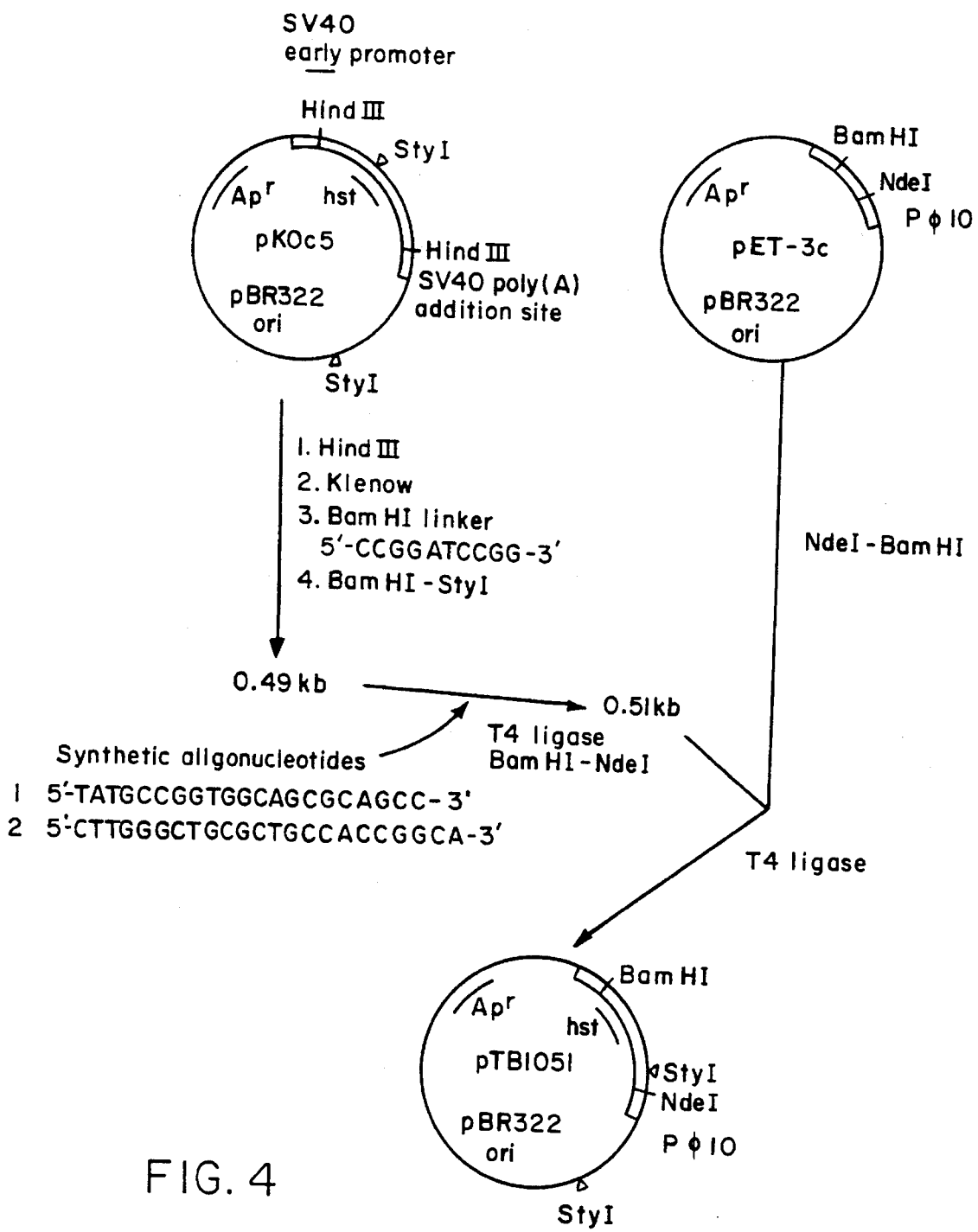
FIG. 4 is a schematic representation showing the construction of plasmid pTB1051 obtained in Reference Example.

M. Taira et al., *Proc. Natl. Acad. Sci.* U.S.A., 84, 2980–2984 (1987) described above taught that the hst-1 gene product is a peptide having an amino acid sequence consisting of 206 amino acids. This amino acid sequence is shown in FIG. 1 (SEQ ID NO:1). However, Delli Bovi et al. disclose in *Molecular and Cellular Biology*, 8, 2933–2941 (1988) that expression in monkey COS-1 cells (wherein the desired product was called K-FGF) provides an amino acid sequence in which 30 or 31 amino acids are eliminated from the N-terminus. A mature protein of the hst-1 is therefore considered to have an amino acid sequence (SEQ ID NO:2) in which 31 amino acids can be eliminated from the N-terminus of the above-mentioned amino acid sequence consisting of 206 amino acids.

The muteins of the present invention include a derivative obtained by deletion, substitution or addition of at least one amino acid, or by addition of at least one sugar chain, lipid or acetyl group, as long as it has hst-1 activity.

The biological activity of the hst-1 protein of the present invention can be assayed, for example, by measuring the stimulation of DNA synthesis of mouse BALB/c3T3 cells based upon the uptake of [³H] thymidine in accordance with the method of Sasada et al. [*Mol. Cell. Biol.*, 8, 588–594 (1988)], measuring the growth promotion of the vascular endothelial cells in accordance with the method of Tada et al. [*Journal of Immunological Methods*, 93, 157 (1986)], or measuring the angiogenesis on the avian embryo allantois in accordance with the method of Auerbach [*Developmental Biology*, 41, 391 (1974)].

Further, MK-CSF activity can be assayed, for example, by cultivating mouse bone marrow cells and measuring the number of megakaryocytes in accordance with the method of Ishibashi et al. [*Proc. Natl. Acad. Sci. U.S.A.*, 86, 5953–5957 (1989)]. Thus, as long as a mutein shows at least one of these activities it is considered as coming within the definition of a hst mutein. Preferably, the activity shown is MK-CSF activity. The mutein should preferably show at least 20% of the activity of the mature hst-1, more preferably, at least 50% of such activity, still more preferably at lease 70% of such activity.

The deletion type muteins of the present invention can include a derivative in which at least one amino acid is deleted from the hst-1-constituent amino acids and which has hst-1 activity. In the deletion type mutein, up to 47 amino acids can preferably be deleted at the N-terminal end from the continuous hst-1-constituent amino acids, and up to 43 amino acids at the N-terminal end are more preferably deleted. Most preferably, up to 27 amino acids at the N-terminal end are deleted. Examples thereof include hst-1 mutein N27 described in Japanese Patent Unexamined Publication No. 3-218393 in which 27 amino acids are deleted from the N-terminus. The deletion type mutein of the present invention may also be a derivative in which at least one of the constituent amino acids is deleted and at least one other amino acid is further substituted.

In methods for producing the hst-1 or the muteins thereof that can be used in the present invention, animal cells, insect cells or microorganisms are preferably infected with expression vectors into which the DNA sequences coding for the hst-1 or the muteins thereof are introduced to produce the hst-1 or the muteins.

The expression vector containing the nucleotide sequence coding for the hst-1 or the mutein thereof of the present invention can be prepared, for example, by the following process:

(i) RNA coding for an hst-1 protein is isolated;

(ii) Single stranded complementary DNA (cDNA) is synthesized against the RNA, followed by synthesis of double stranded DNA;

(iii) The complementary DNA is introduced into a plasmid;

(iv) A host cell is transformed with the recombinant plasmid thus obtained;

(v) After cultivation of the transformant thus obtained, the plasmid containing the desired DNA is isolated from the transformant by an appropriate method such as colony hybridization using a DNA probe;

(vi) The desired cloned DNA is cut out from the plasmid;

(vii) Deletion fitting the purpose is conducted on the cloned DNA;

(viii) An oligonucleotide containing an ATG codon is bound thereto in some cases; and (ix) The resulting DNA is ligated downstream and operably linked to an appropriate promoter for the host cell. The appropriate promoter can readily be selected by the skilled artisan.

The RNA coding for the hst-1 can be obtained from cells of various human cancers such as stomach cancer, colon cancer, hepatic cancer, Kaposi sarcoma and human germinoblastic tumor, and 3T3 transformants with human hst- 1 genes.

Methods for preparing the RNA from the human cancers include the guanidine thiocyanate method [J. M. Chirgwin et al., *Biochemistry*, 18, 5294 (1979)] and the like.

Using the RNA thus obtained as a template, cDNA is synthesized. Alternatively, it can be chemically synthesized according to the reported sequences. The cDNA is introduced, for example, into λ phage vector λgt10 [T. V. Huynh et al. *DNA Cloning A Practical Approach*, p.79, IRL Press Oxford (1985)], for example, in accordance with the method of Watson and Jackson [C. J. Watson and J. F. Jackson, *DNA Cloning A Practical Approach*, p.49, IRL Press Oxford (1985)], and *Escherichia coli* such as C600 and Hf1A [T. V. Huynh et al., ibid.] is infected therewith, whereby a cDNA library can be produced.

Desired clones are selected from the cDNA library thus obtained by known methods such as the plaque hybridization method [T. Maniatis et al., *Molecular Cloning*, p.320, Cold Spring Harbor Laboratory (1982)] and the DNA nucleotide sequence determination method [*Proc. Natl. Acad. Sci. U.S.A.* 74, 560 (1977); *Nucl. Acids Res.* 9, 309 (1981)].

Then, the phage clones are collected, and phage DNA is extracted, for example, by the method of Davis et al. [Davis et al., *Advanced Bacterial Genetics*, Cold Spring Harbor Laboratory (1980)]. A cDNA portion thereof is cut out by use of a restriction enzyme, and introduced into a plasmid such as pUC13. For example, this plasmid can be conveniently used.

The plasmid having the DNA containing the nucleotide sequence coding for the above-mentioned cloned hst-1 can be used as it is or after digestion with a restriction enzyme if desired.

The cloned gene is ligated downstream from a promoter in a vehicle (vector) suitable for expression, whereby an expression vector can be obtained.

In order to produce the hst-1 muteins used in the present invention, in addition to the conventional recombinant DNA technique, site-directed mutagenesis can be employed. Site-directed mutagenesis is well known and described in R. F. Lather and J. P. Lecoq, *Genetic Engineering*, p.31–50, Academic Press (1983). Mutagenesis directed to oligonucleotide is described in M. Smith and S. Gillam, *Genetic Engineering: Principles and Methods*, vol. 3, p.1–32, Plenum Press (1981).

When it is intended to obtain a mutein in which at least one hst-1-constituent amino acid is deleted, three methods preferably are considered for producing a mutagenized hst-1 gene. The first is by a deletion from the amino terminus of the hst-1, the second is by a deletion from the central portion of the hst-1, and the third is by a deletion from the carboxyl terminus of the hst-1.

When the amino terminus is deleted, after deletion of initial start codon ATG, the last codon of an amino acid sequence to be deleted is mutagenized to ATG by use of site-directed mutagenesis, and a recognition site for an appropriate restriction enzyme is formed on the 5'-terminal side of the codon for ease of ligation with a promoter, or the amino terminus of the gene is deleted with a restriction enzyme to ligate an oligonucleotide having ATG with the gene, and adjusting the ATG of the oligonucleotide to the appropriate reading frame by standard techniques.

When the central portion of the amino acid sequence is deleted, recognition sites for a unique restriction enzyme can be formed on the 5'- and 3'-terminal sides of a gene coding for the sequence to be deleted, using site-directed mutagenesis, and these sites are digested with an enzyme to remove the central portion. Ligation of both the resulting fragments provides a gene coding the hst-1 in which the desired central amino acid(s) is deleted. Deviation of a reading frame caused by digestion with the enzyme should be avoided and can readily be avoided by techniques well known in the art.

When the carboxyl terminus of the amino acid sequence is deleted, a codon of a gene coding for the initial codon in the sequence to be deleted is mutagenized to a stop codon by site-directed mutagenesis.

The cloned gene is ligated downstream from a promoter in a vehicle (vector) suitable for expression, whereby an expression vector can be obtained.

Examples of the vehicles (vectors) for preparing recombinant vectors include plasmids pBR322 [*Gene*, 2, 95 (1977)], pBR325 [*Gene*, 4, 121 (1978)], pUC12 [*Gene*, 19, 259 (1982)] and pUC13 [*Gene*, 19, 259 (1982)], which are derived from *E. coli*; plasmids pUB110 [*Biochemical and Biophysical Research Communication* 112, 6678 (1983)], pTP5 and pC194, which are derived from *Bacillus subtilis*, plasmids derived from yeast such as pSH19 and pSH15, bacteriophages such as λ phage, and animal viruses such as retroviruses and vaccinia viruses.

The gene may have ATG as a translation initiation codon at the 5'-terminus thereof, and TAA, TGA or TAG as a translation termination codon at the 3'-terminus thereof. A promoter is further ligated upstream therefrom and operably linked thereto to express the gene. The promoter used in this expression may be any as long as it is suitable for expression in a host selected for the gene expression.

When the host used for transformation is Escherichia, it is preferred to use a trp promoter, a lac promoter, a rec promoter, a λpL promoter, a lpp promoter, a T7 promoter, etc. When the host is Bacillus, it is preferred to use an SPO1 promoter, an SPO2 promoter, penP promoter, etc. When the host is yeast, it is preferred to use a PHO5 promoter, a PGK promoter, a GAP promoter, an ADH promoter, etc. It is preferred that the host is Escherichia, and that the promoter is the trp promoter or the T7 promoter, among others. When the host is an animal cell, a SV40-derived promoter, a retrovirus promoter, etc. can be used. The SV40-derived promoter is particularly preferable.

By using the DNA-containing vector thus constructed, the transformant is prepared.

The host cells that can be used include Escherichia, Bacillus, yeast and animal cells.

Examples of Escherichia described above include *E. coli* K12DHI [*Proc. Natl. Acad. Sci. U.S.A.*, 60, 160 (1968)], M103 [*Nucl. Acids Res.*, 9, 309 (1981)], JA221 [*J. Mol. Biol.*, 120, 517, (1978)], HB101 [*J. Mol. Biol.*, 41, 459 (1969)] and C600 [*Genetics*, 39, 440 (1954)].

Examples of Bacillus described above include *Bacillus subtilis* MI114 [*Gene*, 24, 255 (1983)] and 207-21 [*J. Biochem.*, 95, 87 (1984)].

Examples of the yeast described above include *Saccharomyces cereviciae* AH22R, NA87-11A and DKD-5D.

Examples of the animal cells, cell lines preferably used include monkey cell COS-7 [*Cell*, 23, 157 (1981)], vero, Chinese hamster cell CHO, mouse L cell and human FL cell.

The transformation of Escherichia is carried out, for example, according to the method described in *Proc. Natl. Acad. Sci. U.S.A.*, 69, 2110 (1972) and *Gene*, 17, 107 (1982). The transformation of Bacillus is carried out, for example, according to the method described in *Molecular & General Genetics*, 168, 111 (1979). The transformation of the yeast is carried out, for example, according to the method described in *Proc. Natl. Acad. Sci. U.S.A.*, 75, 1929 (1978). The transformation of the animal cells is carried out, for example, according to the method described in *Virology*, 52, 456 (1973).

Thus, the transformants are obtained by transforming with the vectors containing for example deletion type mutein cDNA of the hst-1.

When bacterial transformants are cultivated, a liquid medium is appropriate as a medium used for cultivation. Carbon sources, nitrogen sources, inorganic compounds and others necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast extracts, vitamins, growth promoting factors and the like may be further added thereto. The pH of the medium is preferably about 6 to about 8.

As the medium used for cultivation of Escherichia, for example M9 medium containing glucose and Casamino Acids [Miller, *Journal of Experiments in Molecular Genetics*, 431–433, Cold Spring Harbor Laboratory, New York (1972)] is preferably used. In order to make the promoter act efficiently, a drug such as 3β-indolylacrylic acid may be added thereto if necessary.

When the host is Escherichia, the cultivation is usually carried out at about 15° to about 43° C. for about 3 to about 24 hours with aeration or agitation if necessary. When the host is Bacillus, the cultivation is usually carried out at about 300° to about 40° C. for about 6 to about 24 hours with aeration or agitation if necessary. When yeast transformants are cultivated, examples of the media include Burkholder minimum medium [K. L. Bostian, *Proc. Natl. Acad. Sci. U.S.A.*, 77, 4505 (1980)]. The pH of the medium is preferably adjusted to about 5 to about 8. The cultivation is usually carried out at about 20° to about 35° C. for about 24 to about 72 hours with aeration or agitation if necessary. When animal cell transformants are cultivated, examples of the media include MEM medium [*Science*, 122, 501 (1952)], DMEM medium [*Virology*, 8, 396 (1959)], RPMI1640 medium [*J. Am. Med. Assoc.*, 199, 519 (1967)] and 199 medium [*Proc. Soc. Biol. Med.*, 73, 1 (1950)]. About 5 to about 20% fetal calf serum may be further added thereto. The pH is preferably about 6 to about 8. The cultivation is usually carried out at about 30° to about 40° C. for about 15 to 60 hours, with aeration or agitation if necessary.

The hst-1 or the mutein thereof can be isolated and purified from the above-mentioned culture product, for example, by the following method.

When the hst-1 or the mutein thereof is extracted from the cultivated cells, the cells are collected by methods known in the art after cultivation. Then, the collected cells are suspended in a buffer solution containing a protein denaturant such as guanidine hydrochloride to elute the desired protein out of the cells. The cells can also be disrupted by a French press, ultrasonic treatment, lysozyme and/or freeze-thawing, followed by centrifugation to obtain the deletion type mutein of the hst-1. A combination of lysozyme and ultrasonic treatment is preferably used.

The hst-1 or the mutein thereof can be purified from a supernatant by an appropriate combination of known separating and purifying methods. These known separating and purifying methods include methods utilizing solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange chromatography, methods utilizing specific affinity such as affinity chromatography, methods utilizing a difference in hydrophobicity such as reverse phase high performance liquid chromatography, and methods utilizing a difference in isoelectric point such as isoelectro-focussing electrophoresis.

More specifically, the above-mentioned supernatant can be subjected to ion-exchange chromatography using DEAE cellulose, thereby being able to remove contaminants such as nucleic acids and acidic proteins. For example, it is effective to subject the supernatant to a DEAE cellulose column equilibrated with a buffer such as Tris around neutrality and collect fractions not adsorbed to the column. Further, the deletion type mutein of the hst-1 can be purified by subjecting the supernatant to ion-exchange chromatography using CM cellulose as a carrier to allow the mutein to be adsorbed by the carrier and eluting the mutein by use of a salt solution.

The deletion type mutein of the hst-1 can be directly purified from a cell extract by column chromatography using an acidic resin such as CM Sephadex. For example, the supernatant is subjected to a CM-Sephadex column equilibrated with a weakly acidic buffer (for example, phosphate buffer), which causes efficient purification. After washing the column with the same buffer, the column is eluted with a buffer further containing a salt (for example, NaCl), thereby allowing the hst-1 or the mutein thereof to be eluted. These eluates can be lyophilized after dialysis.

Affinity chromatography using heparin-Sepharose as a carrier can conveniently be applied to the hst-1 or the mutein thereof in *E. coli* extract for purification of the hst-1 or the mutein thereof. For example, the eluate is loaded onto a heparin-Sepharose column equilibrated with a buffer solution around neutrality such as Tris buffer or phosphate buffer. After thorough washing, the column is eluted with a linear gradient of NaCl, thereby permitting the hst-1 or the mutein thereof to be purified.

In particular, heparin columns developed for high performance liquid chromatography (for example, Shodex AF-pak HR-894, Showa Denko) are effective.

As with the above-mentioned heparin-Sepharose column, the eluate is loaded onto the heparin column equilibrated with a buffer solution around neutrality. After thorough washing, the column is eluted with a linear gradient of NaCl. Repeated cycles of this column step can be used for obtaining a highly purified sample. Thus, the hst-1 or the mutein thereof can be recovered as a highly purified sample.

The sample thus obtained can also be dialyzed and lyophilized to yield a dry powder. Further, it is preferred that serum albumin is added to the sample as a carrier for storage, because the sample can be prevented from being adsorbed by a container.

The coexistence of a slight amount of a reducing agent in the purification course or the storage course is suitable for preventing the oxidation of the sample. The reducing agents include β-mercaptoethanol, dithiothreitol and glutathione.

Thus, the hst-1 or the mutein thereof that is obtained is substantially pure and substantially free from a pyrogen and an endotoxin. The substantially pyrogen and endotoxin free product reacts negatively in the limulus lysate test. The substantially pure hst-1 or mutein of the present invention contains the hst-1 or the mutein thereof in an amount of 95% (w/w) or more as a protein content, and more preferably in an amount of 98% (w/w) or more. The polypeptide may have Met at the N-terminus thereof.

The activity of the hst-1 or the muteins thereof thus formed can be assayed by growth promoting effect of known BALB/c3T3 cells.

Further, MK-CSF activity can be assayed by cultivating mouse bone marrow cells and measuring the number of megakaryocytes.

The hst-1 or the muteins thereof can be safely given parenterally or orally as platelet-increasing agents to warm-blooded mammals (such as humans, mice, rats, hamsters, rabbits, dogs and cats), in a powder form as such or as pharmaceutical compositions (such as injections, tablets, capsules, solutions and ointments) with pharmaceutically acceptable carriers, excipients (for example, stabilizers such as human serum albumin and sorbitol) and diluents.

In particular, they are preferably given parenterally as injections.

It is also possible to use them in combination with other platelet-increasing agents, leukocyte-increasing agents (such as G-CSF, M-CSF, CM-CSF and IL-3), immune activators or erythrocyte-increasing agents (such as erythropoietin).

The preparations are preferably formed, for example, in a solution form or in a lyophilized form to use as injections or for injection administration. They can also be prepared as sustained release preparations, depending upon their purpose.

In forming the preparations as pharmaceutical compositions, pharmaceutically acceptable additives, diluents or excipients may be used in accordance with known pharmaceutical manufacturing processes as desired.

For example, aqueous solution agents for injection are prepared by conventional methods, using solvents such as aqueous solvents (for example, distilled water), water-soluble solvents (for example, physiological saline solution and Ringer solution) and oily solvent (for example, sesame oil and olive oil); and additives such as solubilizers (for example, sodium salicylate solution and sodium acetate), buffer solutions (for example, sodium citrate and glycerol), isotonic agents (for example, glucose and invert sugar), stabilizers (for example, human serum albumin and polyethylene glycol), preservatives (for example, benzyl alcohol and phenol) and soothing agents (for example, benzalkonium chloride and procaine hydrochloride) as desired.

Further, for example, solid preparations for injection can be formed by conventional methods, incorporating diluents (for example, distilled water, physiological saline solution and glucose), excipients (for example, carboxymethyl cellulose (CMC) and sodium alginate), preservatives (for example, benzyl alcohol, benzalkonium chloride and phenol) and soothing agents ( for example, glucose, calcium gluconate and procaine hydrochloride).

Furthermore, in forming the preparations, monosaccharides such as glucose, amino acids, various salts, human serum albumin, etc. may be added. In addition, isotonic agents, pH regulators, soothing agents, antiseptics, etc. can be added to prepare the stable, effective preparations.

The platelet-increasing agents of the present invention can be given to the above-deseribed warm-blooded animal at an appropriate dosage (i.e. effective amount) selected from the range of about 1 ng to about 1000 μg/kg of body weight daily, preferably 1 ng to about 100 μg/kg, and more preferably about 0.1 μg to about 100 μg/kg, taking into account the routes of administration, symptoms, etc., in several divided doses as required.

Examples of parenteral administration of the platelet-increasing agents of the present invention include intravenous administration, subcutaneous administration, intramuscular administration, administration in medullary cavity and administration through mucosa. The routes of administration through mucosa include nasal, intraoral and intrarectal routes.

In particular, intravenous administration and subcutaneous administration are preferred.

The platelet-increasing agents of the present invention may be given once a day or in several divided doses or by continuous intravenous drip infusion. They may also be given intermittently, for example, once for every 3 days or once a week.

Further, the platelet-increasing agents of the present invention may be given as sustained release preparations. Examples of such sustained release preparations include microcapsules and imbedding agents. In particular, the sustained release preparations are preferably imbedded subcutaneously to allow the bases to exhibit their effect for a long period of time.

Administration of the platelet-increasing agents of the present invention can increase the number of platelets in the peripheral blood. The platelet-increasing agent of the present invention is administered in single use or in combination use with another agent. Said platelet-increasing agent and another agent may be administer to mammal concurrently or separately.

In chemotherapy of cancers, administration of almost all chemotherapeutics induces a decrease in the number of platelets, which hinders administering the chemotherapeutics in sufficient amounts. The same is true for radiotherapy. A decrease in the number of platelets is observed at about 3 to about 15 days after administration of the chemotherapeutics. The platelet-increasing agents of the present invention shows platelet-increasing action at about 5 to about 10 days after administration, so that they can be given immediately after administration of the chemotherapeutics, or after observation of a decrease in the number of platelets to restore the number of platelets. Furthermore, it can also be administered to increase the number of platelets by giving the platelet-increasing agents of the present invention before administration of the chemotherapeutics.

The platelet-increasing agents of the present invention can increase platelets in number to restore the number of platelets decreased by chemotherapy, thereby enhancing the effect of treatment and restoring patients from serious symptoms. Thus, the platelet-increasing agents of the present invention can be used as anticancer aids.

Examples of anticancer agents used as the chemotherapeutics include alkylating agents (for example, nitrogen mustard N-oxide, cyclophosphamide, melphalan, carboquone, busulfan, nimustine hydrochloride, ranimustine and dacarbazine), antimetabolites (for example, fluorouracil, tegaful, cytarabine, ancitabine hydrochloride, broxuridine, doxifluridine, mercaptopurine, thioinosine and methotrexate), antibiotics (for example, mitomycin, bleomycin, daunorubicin hydrochloride, doxorubicin hydrochloride, pirarubicin hydrochloride, aclarubicin hydrochloride, neocarzinostatin and actinomycin D), plant alkaloids (for example, vincristine sulfate, vindesine sulfate, vinblastine sulfate and etoposide), hormone agents (for example, tamoxifen citrate), and others (for example, procarbazine hydrochloride, mitobronitol, mitoxanton hydrochloride and cisplatin).

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Tdr: Thymidine
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine The transformant obtained in the Reference Example was deposited with the Institute for Fermentation, Osaka, Japan (IFO) and with the Fermentation Research Institute, the Agency of Industrial Science and Technology, the Ministry of International Trade and Industry, Japan (FRI). The accession number and the deposit date are shown in Table 1.

TABLE 1

| Transformant | IFO | FRI |
| --- | --- | --- |
| E. coli MM294(DE3)/ pLysS pTB1051 | IFO 14952 (Sept. 21, 1989) | FERM BP-2621 (Oct. 4, 1989) |

The present invention will be described in more detail with the following Reference Example and Examples. It is understood of course that they are not intended to limit the scope of the invention.

The mutein obtained in the following Reference Example in which amino acids from the N-terminus to amino acid No. 27 are deleted is called hst-1 mutein N27, and its amino acid sequence is shown in FIG. 3 (SEQ ID NO:3).

REFERENCE EXAMPLE a) Construction of an Expression Plasmid

Plasmid pKOc5 containing human hst-1 cDNA [*Proc. Natl. Acad. Sci. U.S.A.*, 84, 2980–2984 (1987)] was cleaved with HindIII, and the end was made flush by the *E. coli* DNA polymerase I-Klenow fragment reaction. A BamHI linker was ligated therewith by the T4 ligase reaction, followed by cleavage with BamHI-StyI to obtain a 0.49-kb DNA fragment. Then, synthetic oligonucleotides 5'TATGCCGGTG-GCAGCGCAGCC3' (SEQ ID NO:4) and 5'CTTGGGCT-GCGCTGCCACCGGCA3' (SEQ ID NO:5) were ligated with the terminal side of the above-mentioned 0.49-kb DNA fragment to obtain a 0.51-kb NdeI-BamHI DNA fragment (containing initiation codon ATG and nucleotide No. 413-916 of human hst-1 cDNA). This fragment was inserted between NdeI-BamHI of expression vector pET3c for *E. coli* having a $\phi$10 promoter of T7 phage [*Gene*, 56, 125–135 (1987)] to obtain pTB1051 (FIG. 4).

b) Expression of the cDNA in *E. coli*

An RNA polymerase gene of T7 phage was introduced into a strain of *E. coli* MM294 to obtain $\lambda$ phage DE3 [F. W. Studier et al., *J. Mol. Biol.*, 189, 113–130 (1986)], which was lysogenized. Plasmid pLysS having a lysozyme gene of T7 phage [F. W. Studier et al., *J. Mol. Biol.*, 189, 113–130 (1986)] was further introduced thereinto to prepare a strain of *E. coli* MM294(DE3)/pLysS.

The plasmid pTB1051 obtained in (a) described above was introduced into the *E. coli* MM294(DE3)/pLysS to prepare *E. coli* MM294(DE3)/pLysS·pTB1051 (IFO 14952, FERM BP-2621). The resulting cells were cultivated in L medium containing 10 µg/ml chloramphenicol and 35 µg/ml ampicillin, and isopropyl $\beta$-D-thiogalactopyranoside (IPTG) was added to give a final concentration of 0.4 mM at the time when the Klett value reached about 120. Then, cultivation was further continued for 4 hours. The cells were collected by centrifugation and washed with phosphate buffered saline (PBS) cooled with ice. Then, the cells were recollected and stored at $-20°$ C. until they are to be used.

c) Purification of Recombinant Hst-1 Mutein

The cells collected from the 10-liter culture were suspended in 250 ml of 10 mM Tris-HCl (pH 7.4), 10 mM EDTA, 0.5M NaCl, 10% sucrose and 1 mM PMSF cooled with ice, and egg white lysozyme was added thereto to yield a concentration of 0.5 mg/ml. After standing in ice for 1 hour, the suspension was incubated at 37° C. for 5 minutes, and subjected to ultrasonic treatment (for 20 seconds, twice) and centrifugation (SORVALL, at 18 krpm at 4° C. for 30 minutes) to obtain a supernatant as a cell extract.

250 ml of the cell extract was loaded onto a Q Sepharose (Pharmacia) column (5 cm in diameter×5 cm) equilibrated with a solution of 20 mM Tris-HCl (pH 7.6) and 0.5M NaCl, thereby removing nucleic acid components in the extract. A solution flowing through the column (fractions not adsorbed to the Q Sepharose column: 450 ml) was combined with column washings of the solution of 20 mM Tris-HCl (pH 7.6) and 0.5M NaCl. This fraction was subjected to a high performance liquid chromatography apparatus (Gilson) equipped with a heparin column, Shodex AF-pnK HR-2094 (2 cm ID×25 cm, Showa Denko). The column was washed with a solution of 20 mM Tris-HCl (pH 7.6), and then with a solution of 20 mM Tris-HCl (pH 7.6) and 0.5M NaCl. Thereafter, the column was eluted with a linear gradient of 0.5 to 2M NaCl in 20 mM Tris-HCl buffer (pH 7.6) at a flow rate of 6.0 ml/minute for 180 minutes.

Figure 5:
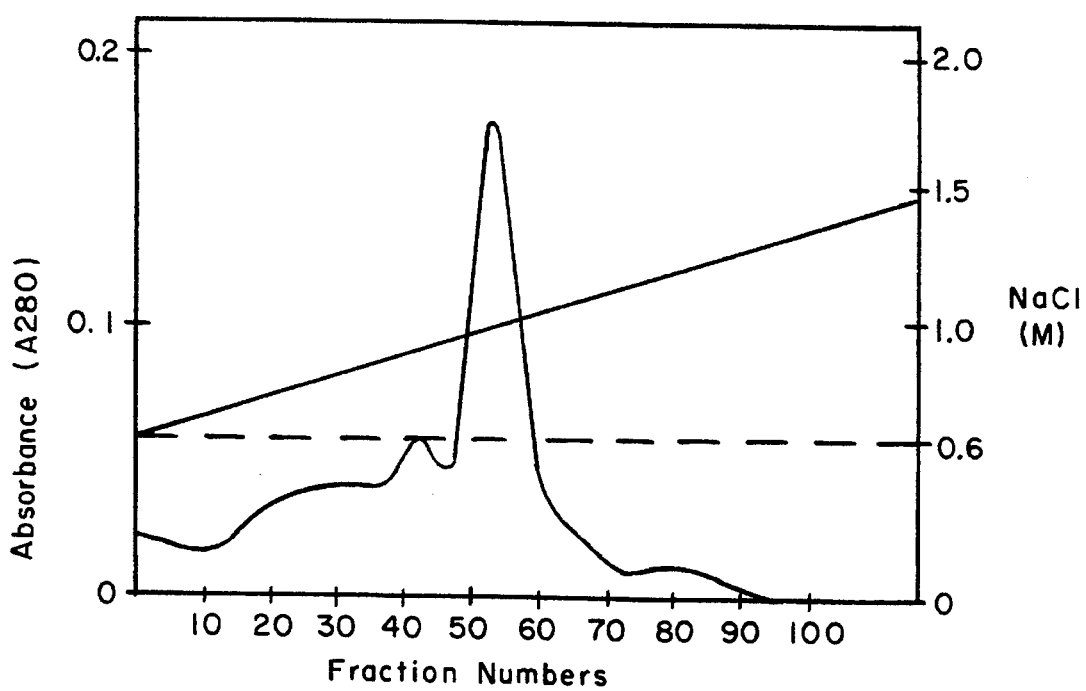
FIG. 5 shows an elution pattern obtained in Reference Example.
Figure 6:
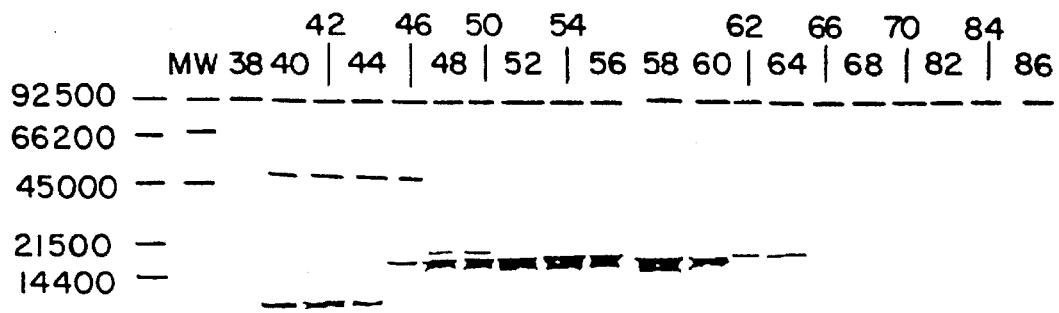
FIG. 6 shows patterns of SDS-PAGE obtained in Reference Example.

The elution pattern is shown in FIG. 5. Referring to FIG. 5, the numbers on the ordinates indicate the absorbance at $OD_{280}$ and the concentration of NaCl in the gradient, and the numbers on the abscissa indicate the fraction number. The gradient elution was initiated at time 0. Fractions for every 0.75 minute were dispersed. The specific activity of the protein contained in these fraction and the amount of the hst-1 mutein recovered are shown in Table 2. The patterns of SDS-PAGE (12.5% polyacrylamide gel) of the respective fractions giving peaks are shown in FIG. 6.

TABLE 2

|  | Protein (mg) | Hst-1 Activity (mg, bFGF equivalent) |
|---|---|---|
| Crude extract | 2530 | 3.8 |
| Fractions not adsorbed to Q Sepharose | 2240 | 5.2 |
| Heparin column elution fractions (47–60) | 6.5 | — |

—: Unmeasured d) Reverse C4 HPLC

Figure 7:
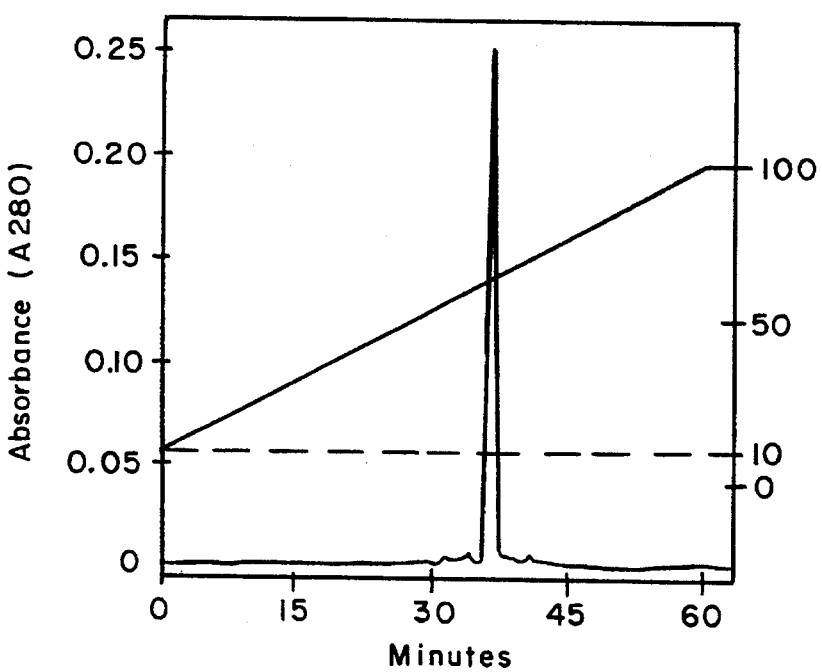
FIG. 7 shows an elution pattern obtained in Reference Example.
Figure 8:
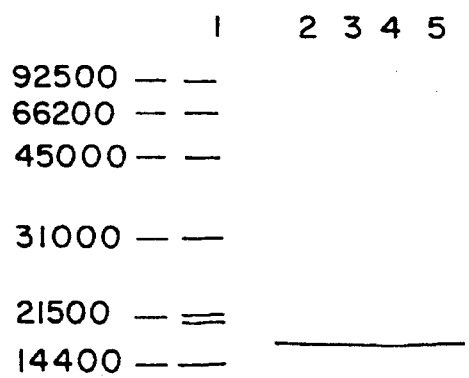
FIG. 8 shows patterns of SDS-PAGE obtained in Reference Example.

About half (300 µg of protein) of the amount of fraction 56 eluted from the heparin HPLC column was applied to a reverse C4 column (YYDAC), and eluted with a linear gradient of 0 to 90% acetonitrile to examine elution patterns. The elution was effected at a flow rate of 1 ml/minute for a gradient time of 60 minutes (FIG. 7). FIG. 8 shows the patterns of SDS-PAGE (12.5% polyacrylamide gel) of peak fractions detected at 36 to 37 minutes as well as that of fraction 56 eluted from the heparin column.

Referring to FIG. 8, the numeral 1 indicates the pattern of 12.5% polyacrylamide gel electrophoresis of a molecular weight marker (50 ng), the numeral 2 indicates that of fraction 56 (50 ng) eluted from the heparin HPLC column, the numeral 3 indicates that of fraction 56 (100 ng) eluted from the heparin HPLC column, the numeral 4 indicates that of the reverse HPLC elution fraction (50 ng), and the numeral 5 indicates that of the reverse HPLC elution fraction (100 ng). The specific activity of the protein contained in these fractions was measured as 0.43, when that of recombinant human bFGF (rhbFGF) (European Patent Unexamined Publication No. 237,966) was taken as 1.00. Changes in specific activity in these purification courses and the amount of hst-1 mutein N27 recovered are shown in Table 3. In Table 3, the specific activity is shown, taking the activity of bovine pituitary gland-derived FGF (Takara Shuzo) as 1.

Thus, hst-1 mutein N27 having the amino acid sequence shown in FIG. 3 was obtained.

TABLE 3

|  | Protein (mg) | Specific Activity | Recovery (%) |
|---|---|---|---|
| Cell extract | 2530 | 0.013 | 100 |
| Fractions not adsorbed to Q Sepharose | 2152 | 0.014 | 91 |
| Heparin column elution fractions | 11 | 0.54 | 18 | e) Biological Activity

The activity of the hst-1 mutein was assayed by measuring the DNA synthesis induction of mouse BALB/c3T3 cells based upon the uptake of [$^3$H] thymidine in accordance with the method of Sasada et al. [*Mol. Cell. Biol.*, 8, 588–594 (1988)]. The results are shown in Table 2 given above.

EXAMPLE 1

MK-CSF Activity of Hst-1 Mutein

Bone marrow cells collected from the femurs of BALB/c mice (female, 7 weeks old) were suspended in IMDM medium (Flow) containing 10% fetal calf serum (FCS) at $2\times10^5$ cells/ml, and incubated on a plastic plate at 37° C. for 45 minutes. Non-adhesive cells were collected and washed with IMDM medium to remove the serum. These non-adhesive bone marrow cells ($1\times10^5$ cells/ml) were suspended in IMDM medium containing Neutridoma-sp (Boehringer Mannheim), and a 96-well flat-bottomed plate (NUNC) was inoculated with 200 μl/well of the suspension.

At this time, hst-1 mutein N27 was added at various concentrations.

After cultivation at 37° C. for 7 days, 50 μl of 5% glutaraldehyde (Wako Pure Chemical Industries) was added, and the plate was centrifuged at 2,000 rpm for 5 minutes to fix the cells. The plate was briefly washed with 0.1M phosphate buffer (pH 6.0), followed by acetylcholine staining. Namely, 30 mg of acetylthiocholine iodide (SIGMA) was dissolved in 45 ml of 0.1M phosphate buffer, and then, 6 ml of 30 mM copper sulfate, 3 ml of 0.1M sodium citrate and 6 ml of 5 mM potassium ferricyanide were added thereto to prepare a staining solution at the time of use. To each well was added 200 μl of the solution, and staining was carried out at room temperature for 6 hours. After washing with 0.1M phosphate buffer, the number of megakaryocytes was counted under a inverted microscope.

Figure 9:
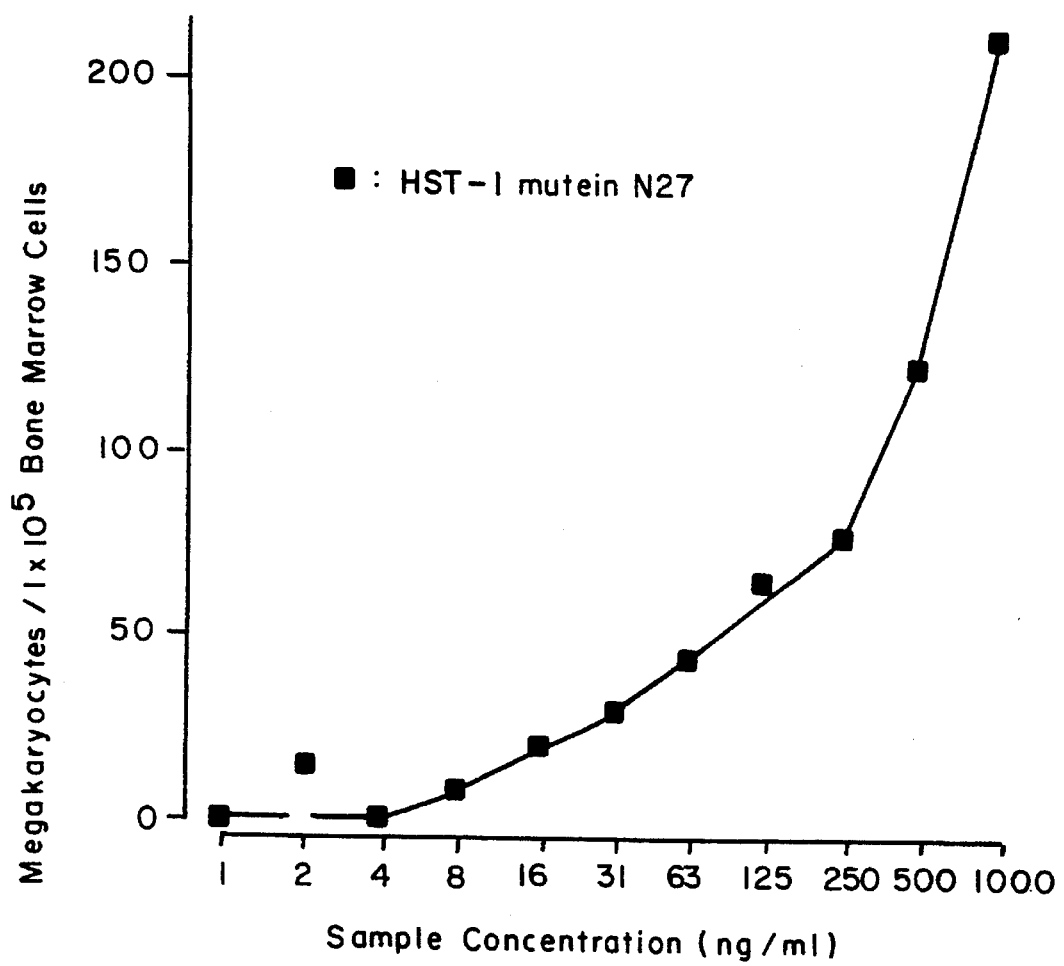
FIG. 9 shows the MK-CSF activity of hst-1 mutein N27 obtained in Example 1.

As shown in FIG. 9, hst-1 mutein N27 stimulated the proliferation of megakaryocyte precursor cells in the mouse bone marrow, in a dose dependent manner.

EXAMPLE 2

Increase of Peripheral Blood Platelets by Administration of Hst-1 Mutein

Hst-1 mutein N27 was dissolved in bovine serum albumin [physiological saline (Otsuka Pharmaceutical) containing 100 μg/ml of BSA (Armer)] to yield a concentration of 500 μg/ml to prepare a preparation of the present invention. BALB/c mice (female, 7 weeks old, Charles River) were subcutaneously given 100 μl of this preparation three times a day for 2 days. As a control, physiological saline containing 100 μg/ml of BSA was given. The blood was collected at 10 days after initial dosing, and the number of platelets in the peripheral blood was counted by use of a multipurpose automatic hemocytometer (Sysmex).

Figure 10:
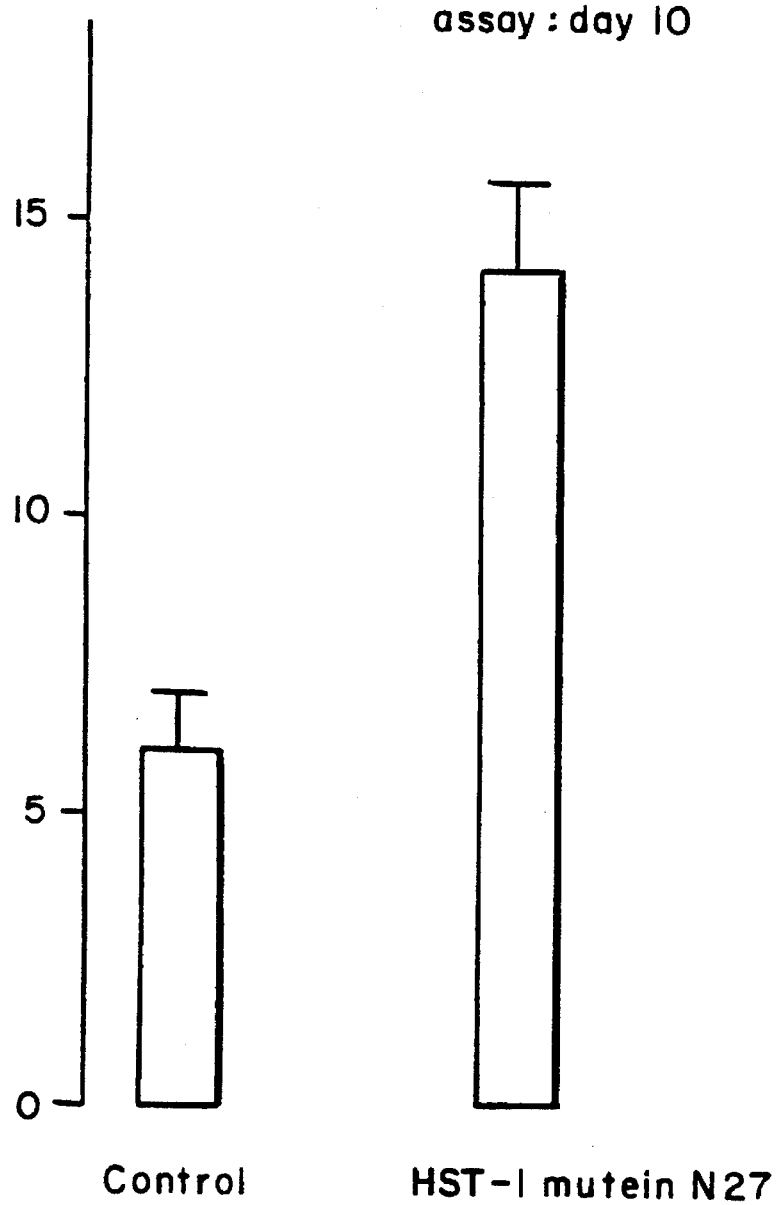
FIG. 10 shows the mouse platelet-increasing action of hst-1 mutein N27 obtained in Example 2.

As a result, the group given hst-1 mutein N27 exhibited a clear increase in the number of platelets in the peripheral blood (FIG. 10). Accordingly, hst-1 mutein N27 has the activity for increasing the number of platelets in vivo, and is available as the platelet-increasing agent.

The platelet-increasing agents containing the hst-1 or the muteins thereof of the present invention can be advantageously used against thrombocytopenia or a reduction in the number of platelets in treating cancers as curative medicines.

EXAMPLE 3

The hst-1 mutein prepared in Reference Example was dialyzed overnight against 50 mM citrate buffer (pH 5.0), followed by preparation of a solution having a concentration of 500 μg/ml. The solution was sterilized through filtration, and 1 ml of the resulting solution was poured into each vial to prepare a preparation for injection. This preparation was stable over a period of 1 year when it was stored at −800° C.

---

What is claimed is:

1. A method of increasing platelet production in mammals which comprises administration to the mammal of an effective amount of a deletion mutein of a heparin-binding secretory transforming factor 1 protein (hst-1), where the deletion mutein has SEQ ID NO:3.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 206 amino acids
      ( B ) TYPE: amino acid
      ( D ) TOPOLOGY: linear ( i i ) MOLECULE TYPE: protein ( x i ) SEQUENCE DESCRIPTION: SEQ ID NO:1:

```
Met  Ser  Gly  Pro  Gly  Thr  Ala  Ala  Val  Ala  Leu  Leu  Pro  Ala  Val  Leu
 1              5                        10                       15

Leu  Ala  Leu  Leu  Ala  Pro  Trp  Ala  Gly  Arg  Gly  Gly  Ala  Ala  Ala  Pro
               20                        25                       30

Thr  Ala  Pro  Asn  Gly  Thr  Leu  Glu  Ala  Glu  Leu  Glu  Arg  Arg  Trp  Glu
               35                        40                       45

Ser  Leu  Val  Ala  Leu  Ser  Leu  Ala  Arg  Leu  Pro  Val  Ala  Ala  Gln  Pro
      50                        55                       60

Lys  Glu  Ala  Ala  Val  Gln  Ser  Gly  Ala  Gly  Asp  Tyr  Leu  Leu  Gly  Ile
 65                       70                       75                       80
```

```
Lys  Arg  Leu  Arg  Arg  Leu  Tyr  Cys  Asn  Val  Gly  Ile  Gly  Phe  His  Leu
                85                  90                            95

Gln  Ala  Leu  Pro  Asp  Gly  Arg  Ile  Gly  Gly  Ala  His  Ala  Asp  Thr  Arg
               100                      105                      110

Asp  Ser  Leu  Leu  Glu  Leu  Ser  Pro  Val  Glu  Arg  Gly  Val  Val  Ser  Ile
          115                      120                      125

Phe  Gly  Val  Ala  Ser  Arg  Phe  Phe  Val  Ala  Met  Ser  Ser  Lys  Gly  Lys
     130                      135                      140

Leu  Tyr  Gly  Ser  Pro  Phe  Phe  Thr  Asp  Glu  Cys  Thr  Phe  Lys  Glu  Ile
145                      150                      155                      160

Leu  Leu  Pro  Asn  Asn  Tyr  Asn  Ala  Tyr  Glu  Ser  Tyr  Lys  Tyr  Pro  Gly
                165                      170                      175

Met  Phe  Ile  Ala  Leu  Ser  Lys  Asn  Gly  Lys  Thr  Lys  Lys  Gly  Asn  Arg
               180                      185                      190

Val  Ser  Pro  Thr  Met  Lys  Val  Thr  His  Phe  Leu  Pro  Arg  Leu
          195                      200                      205
```

( 2 ) INFORMATION FOR SEQ ID NO:2:

( i ) SEQUENCE CHARACTERISTICS:
      ( A ) LENGTH: 175 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Pro  Thr  Ala  Pro  Asn  Gly  Thr  Leu  Glu  Ala  Glu  Leu  Glu  Arg  Arg  Trp
1                   5                   10                      15

Glu  Ser  Leu  Val  Ala  Leu  Ser  Leu  Ala  Arg  Leu  Pro  Val  Ala  Ala  Gln
               20                      25                      30

Pro  Lys  Glu  Ala  Ala  Val  Gln  Ser  Gly  Ala  Gly  Asp  Tyr  Leu  Leu  Gly
          35                      40                      45

Ile  Lys  Arg  Leu  Arg  Arg  Leu  Tyr  Cys  Asn  Val  Gly  Ile  Gly  Phe  His
     50                      55                      60

Leu  Gln  Ala  Leu  Pro  Asp  Gly  Arg  Ile  Gly  Gly  Ala  His  Ala  Asp  Thr
65                      70                      75                       80

Arg  Asp  Ser  Leu  Leu  Glu  Leu  Ser  Pro  Val  Glu  Arg  Gly  Val  Val  Ser
                85                      90                      95

Ile  Phe  Gly  Val  Ala  Ser  Arg  Phe  Phe  Val  Ala  Met  Ser  Ser  Lys  Gly
               100                     105                     110

Lys  Leu  Tyr  Gly  Ser  Pro  Phe  Phe  Thr  Asp  Glu  Cys  Thr  Phe  Lys  Glu
          115                     120                     125

Ile  Leu  Leu  Pro  Asn  Asn  Tyr  Asn  Ala  Tyr  Glu  Ser  Tyr  Lys  Tyr  Pro
     130                     135                     140

Gly  Met  Phe  Ile  Ala  Leu  Ser  Lys  Asn  Gly  Lys  Thr  Lys  Lys  Gly  Asn
145                     150                     155                     160

Arg  Val  Ser  Pro  Thr  Met  Lys  Val  Thr  His  Phe  Leu  Pro  Arg  Leu
                    165                     170                     175
```

( 2 ) INFORMATION FOR SEQ ID NO:3:

( i ) SEQUENCE CHARACTERISTICS:
      ( A ) LENGTH: 148 amino acids
      ( B ) TYPE: amino acid
      ( D ) TOPOLOGY: linear ( i i ) MOLECULE TYPE: protein ( x i ) SEQUENCE DESCRIPTION: SEQ ID NO:3:

```
Pro Val Ala Ala Gln Pro Lys Glu Ala Ala Val Gln Ser Gly Ala Gly
 1               5                   10                  15
Asp Tyr Leu Leu Gly Ile Lys Arg Leu Arg Arg Leu Tyr Cys Asn Val
             20                  25                  30
Gly Ile Gly Phe His Leu Gln Ala Leu Pro Asp Gly Arg Ile Gly Gly
         35                  40                  45
Ala His Ala Asp Thr Arg Asp Ser Leu Leu Glu Leu Ser Pro Val Glu
     50                  55                  60
Arg Gly Val Val Ser Ile Phe Gly Val Ala Ser Arg Phe Phe Val Ala
 65              70                  75                  80
Met Ser Ser Lys Gly Lys Leu Tyr Gly Ser Pro Phe Phe Thr Asp Glu
             85                  90                  95
Cys Thr Phe Lys Glu Ile Leu Leu Pro Asn Asn Tyr Asn Ala Tyr Glu
            100                 105                 110
Ser Tyr Lys Tyr Pro Gly Met Phe Ile Ala Leu Ser Lys Asn Gly Lys
            115                 120                 125
Thr Lys Lys Gly Asn Arg Val Ser Pro Thr Met Lys Val Thr His Phe
    130                 135                 140
Leu Pro Arg Leu
145
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid, synthetic DNA ( x i ) SEQUENCE DESCRIPTION: SEQ ID NO:4:

TATGCCGGTG GCAGCGCAGC C        21

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid, synthetic DNA ( x i ) SEQUENCE DESCRIPTION: SEQ ID NO:5:

CTTGGGCTGC GCTGCCACCG GCA        23